(12) United States Patent
Tsugawa et al.

(10) Patent No.: US 8,252,236 B2
(45) Date of Patent: Aug. 28, 2012

(54) METHOD FOR MEASURING SUBSTRATE CONCENTRATION AND DEVICE FOR THE SAME

(75) Inventors: Wakako Tsugawa, Koganei (JP); Koji Sode, Tokyo (JP)

(73) Assignees: Bioengineering Laboratories, LLC, Shinjuku-ku, Tokyo (JP); Arkray, Inc., Kyoto-shi, Kyoto (JP); Ultizyme International Ltd., Meguro-ku, Tokyo (JP)

( * ) Notice: Subject to any disclaimer, the term of this patent is extended or adjusted under 35 U.S.C. 154(b) by 219 days.

(21) Appl. No.: 12/678,475

(22) PCT Filed: Sep. 18, 2008

(86) PCT No.: PCT/JP2008/002575
§ 371 (c)(1),
(2), (4) Date: Mar. 16, 2010

(87) PCT Pub. No.: WO2009/037840
PCT Pub. Date: Mar. 26, 2009

(65) Prior Publication Data
US 2010/0200429 A1    Aug. 12, 2010

(30) Foreign Application Priority Data
Sep. 18, 2007    (JP) .................................. 2007-241333

(51) Int. Cl.
*G01N 15/06*     (2006.01)
*G01N 33/00*     (2006.01)
*G01N 33/48*     (2006.01)

(52) U.S. Cl. .... 422/82.01; 422/50; 422/68.1; 422/82.02

(58) Field of Classification Search ................ 422/50, 422/68.1, 82.01, 82.02
See application file for complete search history.

(56) References Cited

U.S. PATENT DOCUMENTS

| 4,959,301 A * | 9/1990 | Weaver et al. .................... 435/5 |
| 2005/0214936 A1 | 9/2005 | Bhattacharya |
| 2006/0105418 A1 | 5/2006 | Sato et al. |
| 2007/0131547 A1 | 6/2007 | Nomoto et al. |

FOREIGN PATENT DOCUMENTS

| JP | 2005-013210 | 1/2005 |
| SU | 1814065 | 5/1989 |

(Continued)

OTHER PUBLICATIONS

Kakehi, et al. "A Novel Wireless Glucose Sensor Employing Direct Electron Transfer Principle Based Enzyme Fuel Cell," *Biosensors and Bioelectronics*, vol. 22, pp. 2250-2255, 2007.

(Continued)

*Primary Examiner* — Brian J Sines
(74) *Attorney, Agent, or Firm* — Knobbe, Martens, Olson & Bear, LLP (57) ABSTRACT

The present invention provides a method for measuring a substrate concentration by accumulating an energy resulting from a reaction between a biocatalyst and a substrate recognized by the biocatalyst to a certain level; and using a dependency of an accumulation rate on the substrate concentration as an index; and a apparatus therefor. In particular, the present invention provides a method in which the measurement of the accumulation rate is carried out by measuring a frequency of an energy release in a certain amount of time when the energy accumulated in the capacitor reaches the certain level and is then released.

10 Claims, 10 Drawing Sheets

FOREIGN PATENT DOCUMENTS

| WO | WO 00/46393 | 8/2000 |
|---|---|---|
| WO | WO 2005/093400 | 10/2005 |
| WO | WO 2006/090873 | 8/2006 |

OTHER PUBLICATIONS

Shantaram, et al. "Wireless Sensors Powered by Microbial Fuel Cells," *Environ. Sci. Technol.*, vol. 39, pp. 5037-5042, 2005.

International Search Report dated Oct. 28, 2008 and issued to international application No. PCT/JP2008/002575.

Katz, et al. "Self-Powered Enzyme-Based Biosensors," *Journal of the American Chemical Society*, vol. 123, No. 43, pp. 10752-10753, 2001.

International Preliminary Report on Patentability dated Apr. 7, 2010 and issued to international application No. PCT/JP2008/002575.

Decision on Grant dated Feb. 15, 2012 issued to corresponding Russian patent application No. 2010115257.

Hanashi, et al. "BioCapacitor—A Novel Category of Biosensor," *Biosensors and Bioelectronics*, vol. 24, pp. 1837-1842, 2009.

Rabaey, et al. "Microbial Fuel Cells: Novel Biotechnology for Energy Generation," *TRENDS in Biotechnology*, vol. 23, No. 6, pp. 291-298, Jun. 2005.

Walker, et al. "Biological Fuel Cell and an Application as a Reserve Power Source," *Journal of Power Sources*, vol. 160, pp. 123-129, 2006.

Yuhashi, et al. "Development of a Novel Glucose Enzyme Fuel Cell System Employing Protein Engineered PQQ Glucose Dehydrogenase," *Biosensors and Bioelectronics*, vol. 20, pp. 2145-2150, 2005.

European Search Report dated Oct. 12, 2010 issued to the corresponding European application No. 08831372.1.

* cited by examiner

METHOD FOR MEASURING SUBSTRATE CONCENTRATION AND DEVICE FOR THE SAME

CROSS-REFERENCE TO RELATED APPLICATIONS

This application is the U.S. National Phase under 35 U.S.C. §371 of International Application PCT/JP2008/002575, filed Sep. 18, 2008, which was published in a non-English language, which claims priority to JP 2007-241333, filed Sep. 18, 2007.

TECHNICAL FIELD

The present invention relates to a method for measuring the concentration of a substrate and a device (biosensor) therefor.

BACKGROUND ART

A biosensor is a sensor for measuring a substrate, by a biocatalytic reaction, namely by allowing a biocatalyst to react with a compound, a substrate thereof, which sensor has, as a transducer, a device capable of detecting a product resulting from the biocatalytic reaction, a decreased substrate or a chemical compound generated by a reaction with the product. Or, it means a sensor for measuring the substrate having also, as a transducer, a device capable of detecting physical signals such as a change in light and/or color, or fluorescence, resulting from the biocatalytic reaction. Examples of the biocatalyst include enzymes, organelles, cells and microorganisms.

That is, it can be said that a biosensor is a sensor which converts a biocatalytic reaction into a signal which an electronic device can detect, by using a biocatalyst as a molecular recognition element and by combining a signal thereof with a transducer such as an electrochemical device, optical device or heat detection device, and thereby is capable of analyzing a substrate recognized by the biocatalyst. One of the representative biosensors is an enzyme sensor using an enzyme as a biocatalyst. For instance, for the purpose of measuring glucose (grape sugar), a glucose sensor has been developed, on the basis of a concept, wherein an enzyme oxidizing glucose is immobilized on the surface of an electrode such as an oxygen electrode and a hydrogen peroxide electrode, and the amount of oxygen consumed by an oxidative reaction of glucose and the amount of hydrogen peroxide generated at the same time are electrochemically measured.

Among enzyme sensors widely used at present, a sensor using an oxidoreductase is mainly used. A major principle thereof is based on a method for measuring, with an ampere meter, electrons generated when a reduced substance generated by an enzyme reaction at an anode is re-oxidized by an electric potential externally applied; or a method for measuring by a difference in the electric potentials generated between an anode and a cathode when the generated electrons are reduced at the cathode.

Also, as a method used in a simple blood sugar diagnostic apparatus or the like, a method comprising colorizing a reduced substance generated by an enzyme reaction such as hydrogen peroxide or a reduced artificial electron acceptor in accordance with a conventional method, and determining the color by an optical sensor has been employed.

In addition, as an example of a special enzyme, an enzyme sensor employing a luciferase as an enzyme, which is an enzyme derived from a light-emitting organism such as a firefly, has been also reported, which enzyme sensor is characterized by detecting light generated by an enzyme reaction where a substrate for the luciferase reacts. Yet, as for this method, applications are limited to the cases where a luciferase can be used, such as the cases where the objective is limited to the detection of a substance which is an substrate for the luciferase, such as ATP, or the cases where there can be employed a principle that when an antibody reaction is detected, it can be indirectly detected via an optical signal by labeling the antibody with the luciferase.

Non-patent Literature 1: Katz et al., *J. Am. Chem. Soc.* 2001, 123, 10752-10753

DISCLOSURE OF THE INVENTION

Problems to be Solved by the Invention

In the conventional biosensor described above, a measuring apparatus using a biosensor such as an enzyme sensor (hereinafter referred to as enzyme sensor system) is composed of a measuring part by the biosensor and a monitor part in which a measured signal is received and processed. In major types, these parts are integrated or, as seen in a self-measuring blood sugar diagnostic apparatus, a part corresponding to the measuring part can be detached to be disposable. Also, the measuring part for detecting a substrate concentration and the monitor part for detecting a signal from the biosensor need to be in direct contact with or be wired to a field where the biocatalytic reaction takes place, or require a circuit for actuating a special transmitter and a power supply therefore to be provided, all of which are problematic.

Meanwhile, thus far, an enzyme sensor using an electromotive force of an enzyme fuel cell as an index has been reported. Yet, since the electromotive force of this fuel cell alone is less than 1 V, by the electromotive force of the fuel cell, the fuel cell was not able to operate, as is, a device for sensing. In the case of measuring a substrate concentration using the electromotive force of the fuel cell-type enzyme sensor as an index, it was required that the electromotive force be directly connected to a voltmeter to measure the electric potential, thereby measuring the substrate concentration. Or, it was required that the electromotive force be directly connected to the voltmeter for measuring the electromotive force, and a response value of the voltmeter be transmitted to an external receiver by a wireless device actuated by an external power supply. (See "A Novel Wireless Glucose Sensor Employing Direct Electron Transfer Principle Based Enzyme Fuel Cell", Noriko Kakehi, Tomohiko Yamazaki, Wakako Tsugawa and Koji Sode *Biosensors & Bioelectronics* Epub 2006 Dec. 11).

Thus, although a fuel cell-type enzyme sensor is compact and has a high performance sensing ability, in cases where it is embedded in or mounted on a living body and its signal is attempted to be detected in wireless, data of the fuel cell-type enzyme sensor cannot be read without further providing a power supply. Therefore, in order to increase the electromotive force of an enzyme fuel cell, it is considered that, by connecting the enzyme fuel cells in series, the electromotive force can be increased depending on the number of the fuel cells. However, in cases where power generation in a living body or monitoring in a living body is aimed, disposing the enzyme fuel cells connected in series in the living body complicates the apparatus and requires large electrodes, which were problematic and practically impossible.

Means for Solving the Problems

Therefore, in the present invention, it is proposed that the measurement be carried out by accumulating energy resulting from a biocatalytic reaction such as an enzyme and using, as an index, the accumulation rate or the frequency with which the energy once accumulated is released. Thus, in the present invention, in cases where a certain amount of energy is produced by a biocatalytic reaction depending on the substrate concentration, by paying attention that the production rate thereof depends on the substrate concentration, it is used the fact that if the energy to be accumulated is set to a certain level and the energy is released when the energy is accumulated to the certain level, the frequency of the release depends on the substrate concentration of the biocatalyst. The present invention proposes that the substrate concentration of the biocatalyst be measured by measuring the frequency of the release.

In particular, it is able to provide a method for measuring the concentration of a substrate and a device therefor by combining a biocatalyst such as an enzyme and a device having a circuit in which, by accumulating an electrical energy in a capacitor up to a certain level as energy resulting from a biocatalytic reaction and releasing the energy, a signal is generated depending on the amount of the released electricity.

Also, by combining a circuit which generates light, sonic waves, electromagnetic waves or the like from the electrical energy accumulated in the capacitor, a signal generated from the sensor is able to be readily received by a signal detector in a non-contact monitor part. Therefore, the measuring part and monitor part can be separated. Thus, the separation of the measuring part and monitor part allows the measuring part to be much smaller. Such miniaturization is advantageous in a portable sensor, or a sensor placed or embedded inside a body.

Furthermore, in another aspect of the present invention, provided is a circuit of a novel wireless enzyme sensor capable of accumulating an electrical energy generated by an enzyme reaction in a capacitor, actuating a wireless device by the electromotive force, and transmitting the signal to an external receiver. Thus, provided is a self-propelled wireless enzyme sensor capable of transmitting a signal of a sensor by wireless using an electromotive force of an enzyme fuel cell without a power supply. Also, in the device of the present invention, unlike a conventional measurement of an electric potential or the like, a wireless signal can be detected by a receiving side when the electromotive force exceeds the actuation voltage of a wireless transmitter. Based on this, a device for measuring the concentration of a substrate using the actuation frequency of the wireless transmitter as an index is provided.

The structure of the present invention is as follows:
(1) A method for measuring the concentration of a substrate, the method containing:
    accumulating energy resulting from a reaction between a biocatalyst and a substrate recognized by the biocatalyst to a certain level; and
    measuring the substrate concentration by using as an index the fact that the accumulation rate of the energy is dependent on the substrate concentration.
(2) The method according to above item 1, wherein said index is measured on the basis of the release frequency of the energy in a given period wherein said energy is released when reaching or exceeding said certain level.
(3) The method according to above item 1 or 2, wherein the biocatalyst is an enzyme, an organelle, a microorganism or a cell.
(4) The method according to any one of above items 1 to 3, wherein the reaction catalyzed by the biocatalyst is an oxidation reaction.
(5) The method according to above item 3, wherein the biocatalyst is an enzyme.
(6) The method according to above item 5, wherein the enzyme is an oxidoreductase.
(7) The method according to any one of above items 1 to 6, wherein the energy to be accumulated is accumulated in a capacitor as an electrical charge.
(8) An apparatus for measuring the concentration of a substrate, the apparatus containing:
    a fuel cell having an anode on which a substrate of a biocatalyst is disposed and a cathode on which an external electron acceptor is disposed;
    a capacitor connected to the fuel cell in series; and
    a measuring device for measuring the substrate concentration by using the charging rate of the capacitor as an index;
    wherein an electromotive force generated by transferring electrons generated by a reaction between the substrate and the biocatalyst into the external electron acceptor on the cathode is charged in the capacitor, and the charging rate thereof is measured by the measuring device.
(9) The apparatus according to above item 8, wherein the measuring device measures the discharging frequency, by said capacitor discharging an accumulated electric potential when the electric potential charged in the capacitor reaches or exceeds a certain level.
(10) The apparatus according to above item 8 or 9, further containing a charge pump for charging the capacitor, which charge pump boosts the electromotive force based on the biocatalytic reaction when the capacitor is charged.
(11) The apparatus according to above item 9 or 10, wherein the measuring device has a signal generation circuit generating a signal by the discharging from the capacitor and measures the frequency of the signal.
(12) The apparatus according to above item 11, wherein the signal generation circuit is a wireless transmitter.
(13) The apparatus according to above item 11 or 12, wherein the measuring device measures a physical signal and/or a chemical signal generated when the signal generation circuit is actuated.
(14) The apparatus according to above item 13, wherein the physical signal and/or the chemical signal are/is a sonic wave, light or an electromagnetic wave.
(15) The apparatus according to any one of above items 11 to 14, wherein the measuring device further contains a receiver for receiving the signal generated by the discharging of the capacitor when the capacitor exceeds the actuation voltage of the wireless transmitter by charging.
(16) The apparatus according to any of above items 8 to 15, wherein the biocatalyst disposed on the anode is an enzyme.
(17) The apparatus according to above item 16, wherein the enzyme is an oxidoreductase.
(18) The apparatus according to above item 16, wherein the enzyme catalyzes oxidation of glucose.

As the biocatalyst used in the present invention, enzymes, organelles, cells, microorganisms and the like can be used. Also, as a reaction catalyzed by the biocatalyst, a redox reaction of an object to be measured is preferred. As the enzyme, various oxidoreductases can be used. Examples thereof include oxidases for alcohol, glucose, cholesterol, fructosyl amine, glycerin and uric acid, which oxidases use FAD as a coenzyme; dehydrogenases for alcohol, glucose and glycerin, which dehydrogenases require FAD as a coenzyme; and dehydrogenases for alcohol, glucose and glycerin, which dehydrogenases use PQQ as a coenzyme. In particular, in cases where glucose is to be measured, a glucose oxidase and/or glucose dehydrogenase using FAD or PQQ as a coenzyme is/are preferred. This may be an enzyme isolated and purified from a microorganism or cells which produce the enzyme. Or, it may be a recombinant enzyme produced in *E. coli* or the like.

In addition, the biocatalyst used in the present invention may not be an enzyme alone, but may be a membrane containing the enzyme, an organelle containing the enzyme or a cell containing the enzyme as long as it is able to oxidize a substrate at an anode and transmit this electron to an appropriate electron acceptor or directly to an electrode, and can be used as long as an oxidation reaction of the above-mentioned substrate is achieved by the result of these enzyme reactions and a plurality of enzyme reactions coupled with them.

As the method for generating an electrical energy using an enzyme according to the present invention, an enzyme fuel cell can be employed. That is, it is an enzyme fuel cell characterized in that an oxidase or dehydrogenase is immobilized on an anode.

In this case, as a cathode, an electrode in which an enzyme reducing oxygen such as bilirubin oxidase is used or an electrode in which appropriate electron acceptors are combined can be used. Or, a catalyst having ability to reduce oxygen such as platinum or an inorganic catalyst containing platinum can be used.

Also, a structure containing an electron acceptor as well as the enzyme is thought to be used as an anode. That is, those transferring an electron obtained by an enzyme reaction to an artificial electron acceptor and oxidizing the electron on the electrode can be used. Or, dehydrogenases capable of directly transferring electrons to an electrode such as an enzyme having cytochrome in an electron transport subunit and the like can constitute the anode without adding any artificial electron acceptor. As electrode materials for the anode and cathode, electrodes filled or coated with carbon particles, carbon electrodes, gold electrodes, platinum electrodes, or the like can be used.

The artificial electron acceptor of the anode or cathode is not particularly restricted and an osmium complex, a ruthenium complex, phenazine methosulfate and a derivative thereof, a quinone compound or the like can be used.

The enzyme for the cathode is not particularly restricted, and bilirubin oxidase or laccase can be applied. The artificial electron acceptor of the cathode is not restricted and potassium ferricyanide, ABTS or the like can be used.

As the enzyme for the anode, various oxidases or dehydrogenase can be used. In particular, in cases where glucose is to be measured, glucose oxidase or glucose dehydrogenase using PQQ or FAD as a coenzyme can be used.

In the present invention, as a method for mounting an enzyme on an electrode, a mixture of the enzyme as is and an electrode material such as carbon paste can be used. Or, after preparation by a general method for immobilizing an enzyme, an immobilized enzyme can be mounted on the electrode. Examples include methods in which a cross-linking treatment with a binary cross-linking reagent such as glutaraldehyde is carried out after the mixing of both; and methods of inclusively immobilizing in a synthetic polymer such as a photocrosslinking polymer, electroconductive polymer or redox polymer, or a natural polymer matrix. The thus prepared mixed protein is mixed with carbon particles or mixed with carbon paste which is composed of the carbon particles and is in a mode of being readily combined with an enzyme. Thereafter, the resulting mixture is further subjected to a cross-linking treatment and then mounted on the electrode composed of carbon, gold or platinum. As the carbon particle, one having a specific surface area ranging from about 10 $m^2/g$ to not less than 500 $m^2/g$, more preferably not less than 800 $m^2/g$ can be used. Examples of the former include VULCAN™ (Cabot Corporation) as a commercially available product and examples of the later include Ketchen black™ (Akzo Nobel Chemicals Inc.).

Further, when the enzyme is mounted on the electrode in this manner, an artificial electron acceptor can be immobilized at the same time. Typically, glucose dehydrogenase using FAD as a coenzyme, FADGDH and methoxy phenazine methosulfate (mPMS) are mixed. The mixture is further mixed with carbon paste and then freeze dried. This is mounted on a carbon electrode and the resultant is immersed as is in a glutaraldehyde aqueous solution to cross-link a protein, thereby making an enzyme electrode.

In the enzyme fuel cell, an oxidase or dehydrogenase using a measuring object as a substrate is immobilized on the anode electrode. An oxygen reductase is immobilized on the cathode. The thus prepared electrodes are used as electrodes for the anode and the cathode. In the anode, for example, m-PMS can be used as an artificial electron acceptor and also in the cathode, for example, ABTS can be used as an artificial electron acceptor.

Figure 2:
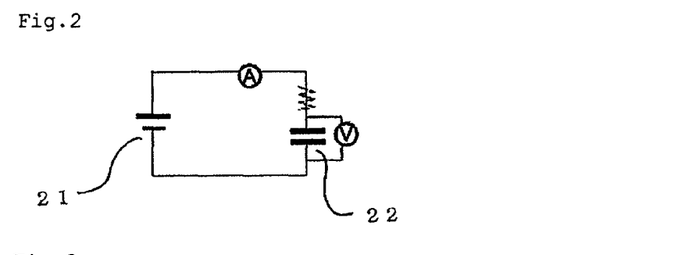
FIG. 2 shows a circuit diagram of a capacitor used in the present invention.

By connecting the thus prepared part where an electrical energy is generated by an enzyme reaction to a capacitor, an electrical energy can be stored. That is, based on an electromotive force obtained by the enzyme reaction, the capacitor connected to the circuit shown in FIG. 2 is charged until the capacity of the capacitor is filled up. Therefore, in cases where the enzyme reaction is carried out in a solution of the same substrate concentration, when a capacitor with a larger capacity is used, it takes a longer period of time to complete charging. Conversely, when a capacitor with a smaller capacity is used, the time to complete charging is shorter. Or, in cases where a capacitor with the same capacity is used, when the substrate concentration of the enzyme is lower, the amount of the electrical energy generated per unit time is smaller and thus the time to complete charging is longer, whereas when the substrate concentration is higher, the time to complete charging is, in contrast, shorter. That is, by setting the capacitor at a certain amount of capacity, the time required for charging varies depending on the concentration of the substrate of the enzyme. Therefore, the substrate concentration can be measured by using the time required for charging (charging rate) as an index. That is, by recording in advance the correlation between the observed time required for charging (charging rate) and the substrate concentration and, based on that, preparing a calibration curve, the substrate concentration of an unknown sample can be measured from the observed time required for charging.

Also, by connecting an appropriate circuit to the capacitor such that discharging begins when charging is completed, the substrate concentration can be measured in the same manner by measuring the charging and discharging frequency per unit time. That is, by recording in advance the correlation between the observed discharging frequency per unit time and the substrate concentration and preparing, based on that, a calibration curve, the substrate concentration of an unknown sample can be measured from the observed discharging frequency.

Further, if light, a sonic wave or an electromagnetic wave is generated by a circuit connecting there, by observing the light, the sonic wave or the electromagnetic wave, and measuring the frequency at which it is observed per unit time or the interval between its observations, the concentration of the substrate can be measured. That is, by recording in advance the correlation between the observed time required for generating the light, the sonic wave or the electromagnetic wave and the substrate concentration and preparing, based on that, a calibration curve, the substrate concentration of an unknown sample can be measured from the observed time required for generating the light, the sonic wave or the electromagnetic wave or an frequency per unit time.

In addition, depending on a circuit to be actuated, it is possible that an electric potential of the capacitor is appropriately set. That is, by combining an electromotive force of an enzyme fuel cell which generates an electrical energy generated by an enzyme reaction as an electromotive force with a booster circuit, the electric potential charged in the capacitor can be increased. For this boosting, a commercially available charge pump or an IC circuit thereof can be used. The electric potential stored in the capacitor can be adjusted depending on the type and the number of the charge pump combined. The electric potential in the capacitor can be set depending on the signal generation circuit to be actuated.

The frequency at which the capacitor is charged and discharged depends, as described above, on the capacity of the capacitor and the concentration of the substrate. That is, if the substrate concentration is constant, the smaller the capacity of the capacitor is, the higher the charging and discharging frequency is. And, the larger the capacity of the capacitor is, the lower the charging and discharging frequency is. Also, if the capacity of the capacitor is constant, the charging and discharging frequency changes depending on the substrate concentration. And, the lower the substrate concentration is, the lower the charging and discharging frequency is. The higher the substrate concentration is, the higher the charging and discharging frequency is.

Figure 3:
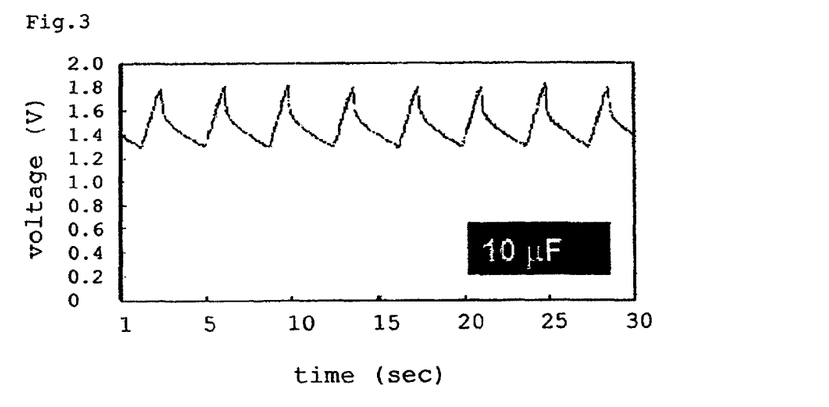
FIG. 3 shows the change in the electric potential by repeated charging and discharging in a capacitor in the apparatus according to the present invention.

For instance, when a voltmeter is connected to both ends of the capacitor, what is observed is shown in FIG. 3. In this mode, a sample of a constant concentration of glucose is used as a substrate; an enzyme catalyzing dehydrogenation of glucose is employed as an enzyme; and an electromotive force generated by an enzyme fuel cell is boosted from 0.3 V of the enzyme fuel cell to 1.8 V through a charge pump, thereby charging the capacitor. As shown in FIG. 3, it can be observed that the electrical potential of the capacitor reaches 1.8 V at regular intervals, and the electrical energy generated from the enzyme reaction is stored and then released. In this case, when the capacity of the connected capacitor is changed from 0.47 µF to 1 µF, the observed charging and discharging interval changes. That is, when the capacity of the capacitor is 0.47 µF, the interval was 0.2 seconds (the charging and discharging frequency 5 times/second, 5 Hz) whereas the frequency changes as follows: 2.4 Hz at 1 µF, 0.27 Hz at 10 µF and 0.028 Hz at 100 µF.

Figure 4:
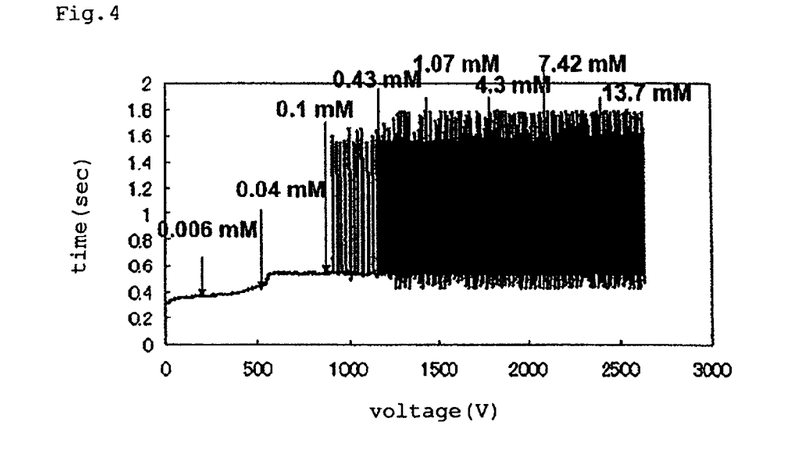
FIG. 4 shows the relationship between the charging frequency of a capacitor and the concentration of glucose.

Further, when a condition where the capacitor is charged, by using a capacitor of 10 µF and changing the concentration of glucose, is observed, the charging and discharging interval is longer at a lower concentration of glucose, and the charging and discharging interval is shorter at a higher concentration of glucose (see FIG. 4). Conversely, when this is observed as a charging and discharging frequency, the charging and discharging frequency is lower at a lower concentration of glucose, and the charging and discharging frequency is higher at a higher concentration of glucose.

By connecting this circuit to a circuit generating a signal depending on charging and discharging of the capacitor in the same manner and observing the light, the sonic wave or the electromagnetic wave generated from there, the substrate concentration can be measured in the same manner. For example, in cases where a light emitting diode is connected, by observing the emission interval of the light emitting diode or the emission frequency, the substrate concentration can be measured.

Figure 5:
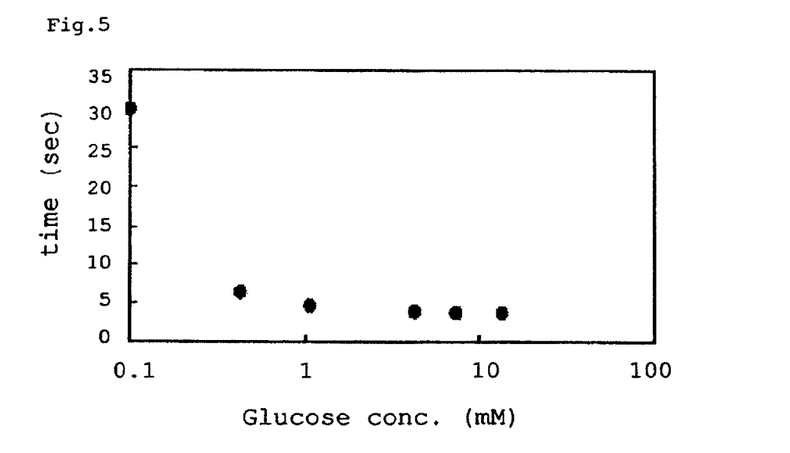
FIG. 5 shows the emission interval (time) of a light emitting diode for the change in the concentration of glucose.

As shown in FIG. 5, the emission interval is longer at a lower concentration of glucose and the emission interval is shorter at a higher concentration of glucose. Conversely, when this is observed as an emission frequency, the emission frequency is lower at a lower concentration of glucose and the emission frequency is higher at a higher concentration of glucose.

Also, in cases where a resonant circuit generating an electromagnetic wave is connected to this circuit, by observing the interval or the frequency of the transmission of the electromagnetic wave, the substrate concentration can be measured. In this case, the interval of the transmitted electromagnetic wave is longer at a lower concentration of glucose and the interval is shorter at a higher concentration of glucose. When this is observed as a transmission frequency of the electromagnetic wave, the transmission is lower at a lower concentration of glucose and the transmission frequency is higher at a higher concentration of glucose.

As can be seen from such a mode, it is evident that, when a signal transmitter actuated by the capacitance and electrical potential of a capacitor is connected, regardless of the type of the signal transmitted from there, that is, light, a sonic wave, or an electromagnetic wave, the concentration of a substrate of an enzyme reaction can be measured by observing the interval and frequency. In addition, it is also evident that the enzyme is not limited to the dehydrogenase using glucose as a substrate which is shown herein, and various oxidases and dehydrogenases can be used. Examples thereof include oxidases for alcohol, glucose, cholesterol, fructosyl amine, glycerin and uric acid, which oxidases use FAD as a coenzyme; dehydrogenases for alcohol, glucose and glycerin, which dehydrogenases use FAD as a coenzyme; and dehydrogenases for alcohol, glucose and glycerin, which dehydrogenases use PQQ as a coenzyme. Even when it is not an enzyme alone, as long as it is able to oxidize a substrate at an anode and transmit this electron to an appropriate electron acceptor or directly to an electrode, it may be a membrane, an organelle, a cell or a microorganism, all of which contain the enzyme. If an oxidation reaction of the above-mentioned substrate is achieved by the result of these enzyme reactions, it can be used, which is self-explanatory from study cases of biosensors using biocatalysts catalyzing various redox reactions.

Also, as another mode, a transmission circuit used in wireless communication can be used as a signal transmission circuit connected to a capacitor. These transmission circuits require a certain level or higher of electric potential for its actuation. If the electromotive force is below this level, the circuit stops and so does the transmission. Also, it cannot be actuated when the electromotive force is not higher than the certain level. That is, when the wireless transmission circuit actuated at 1.5 V is connected to the capacitor and the transmitted signal is observed by a distant reception system, the transmission from the wireless is observed corresponding to charging and discharging of the capacitor. That is, depending on the concentration of a substrate of an enzyme reaction, the wireless transmission circuit is actuated and the signal is transmitted. The interval is longer when the enzyme substrate concentration is lower and the interval is shorter when the enzyme substrate concentration is higher. Also, the transmission frequency of the signal is lower when the enzyme substrate concentration is lower and the transmission frequency of the signal is higher when the enzyme substrate concentration is higher. Therefore, the substrate concentration of enzyme can be measured by observing a received transmission record.

As such a wireless transmission circuit, a resonant circuit may be employed. Also, for a capacitor in this resonant circuit, a capacitor whose capacity is variable may also be employed.

BEST MODE FOR CARRYING OUT THE INVENTION

The present invention will now be described in detail below by way of examples thereof. However, the present invention is not limited to the examples.

EXAMPLE 1

Preparation of Anode

Ketchen black ink (10 mL), 100 mM PPB (pH 7.0) (10 mL) and an FADGDH complex solution (40 mL) (1.2 U/mL) were mixed. And, 50 mL of the mixture was coated uniformly on 1 cm$^2$ of carbon cloth and then air-dried at 4° C. for 3 hours. By immersing the resultant in a 1% glutaraldehyde solution (10 ml) at room temperature for 30 minutes, a cross-linking treatment was carried out. Next, by immersing this carbon cloth in 10 mM Tris-HCl (10 ml) for 20 minutes, unreacted glutaraldehyde was removed. Thereafter, the resultant was immersed in 100 mM PPB (pH 7.0) (10 ml) for 1 hour to be equilibrated, thereby preparing an anode.

Preparation of Cathode:

A platinum supported carbon ink (10 mL) and 100 mM PPB (pH 7.0) (50 mL) were mixed. And, 50 mL of the mixture was coated uniformly on carbon cloth and the resultant was air-dried at 4° C. for 3 hours. To the resultant, 50 mL of 3% (w/v) Poly(dimethylsiloxane) (PDMS) diluted by ethanol was dropped and air-dried overnight to provide a cathode.

Construction of Electrical Cell and Circuit:

Using the prepared anode and cathode, an electrical cell was constructed using 100 mM PPB (pH7.0) containing 20 mM glucose as a reaction solution. The electrical cell, a variable resister, a capacitor and a switch were all connected in series, thereby preparing a circuit.

In the thus prepared circuit, the charging time of the capacitor was examined. Thus, using two types of capacitors (0.1 mF and 1 mF), under the condition where charging was carried out at a glucose concentration of 20 mM, an electric potential applied to the capacitor and an electric current which flows in the circuit when the switch were connected to a resistance were measured to examine the charging time for the capacitor.

Figure 6A:
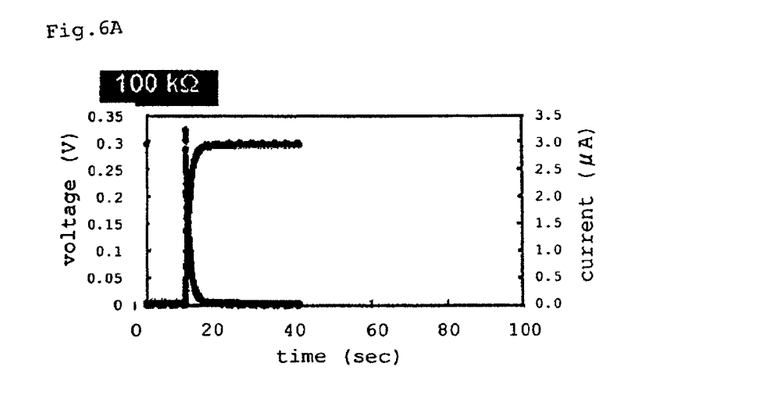
FIG. 6A shows the time required for charging of a capacitor (resistance 100 kΩ).
Figure 6B:
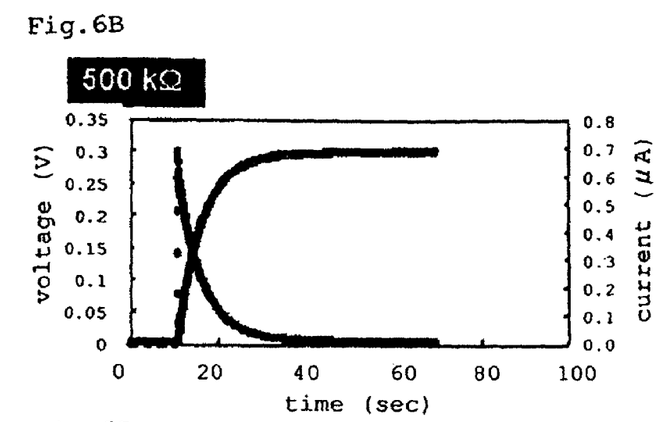
FIG. 6B shows the time required for charging of a capacitor (resistance 500 kΩ).
Figure 6C:
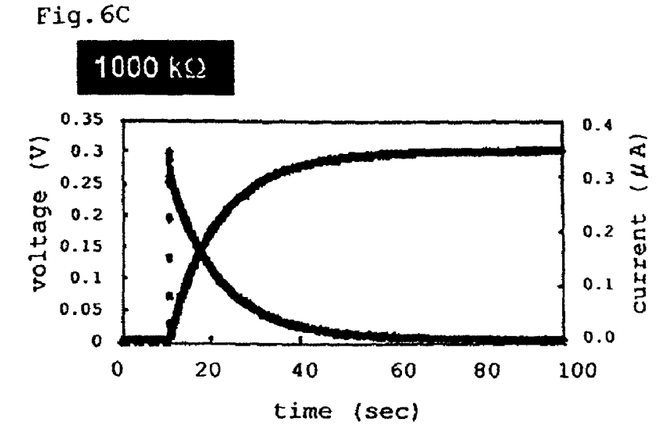
FIG. 6C shows the time required for charging of a capacitor (resistance 500 kΩ).

In this case, the results when the capacitor of 1 mF was used as the capacitor and the resistance was 100 kΩ, 500 kΩ and 1000 kΩ were shown in FIG. 6. The electric current flowed at the same time when the switch was turned on. Also, the electric current decreased over time and the electric potential on the capacitor increased. Further, when the resistance value was changed to decrease or increase the electric current value, the charging time of the capacitor increased or decreased accordingly. At any resistance, when the charge amount charged in the capacitor was calculated from the electric current value which flowed in the circuit, it was almost equal to the capacity of the capacitor. In addition, when the capacitor of 0.1 mF was used, the similar results were obtained. Yet, as compared with the capacitor of 1 mF, the charging time was shorter. It was shown that, even in cases where an enzyme fuel cell was used as a power supply, the capacitor was able to function adequately.

Using a circuit prepared in the same way, a dependency of the charging time of a capacitor on the glucose concentration was evaluated. Using a condenser of 1 mF, the electric potential on the capacitor was measured when a resistance was set to 10 kΩ or 500 kΩ. In this case, by gradually adding a glucose sample to increase the concentration of glucose in a reaction solution, the charging time at each concentration of glucose was examined.

Figure 7A:
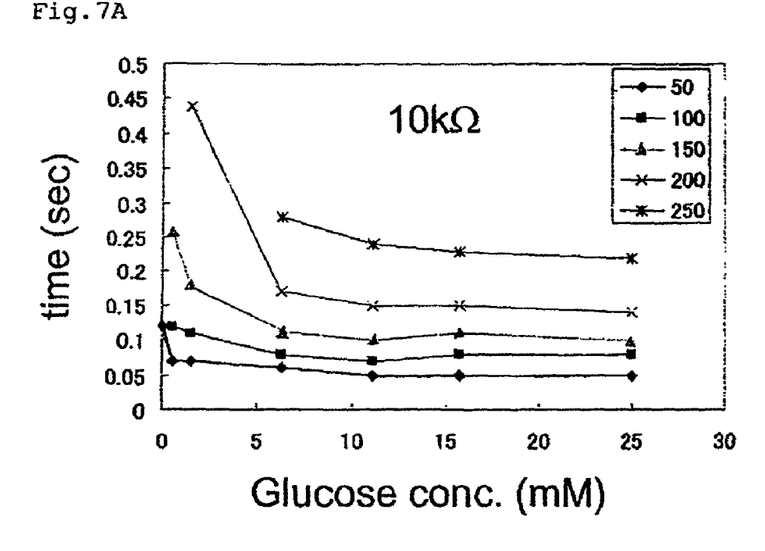
FIG. 7A shows the time required for charging of a capacitor for the change in the concentration of glucose (10 kΩ).
Figure 7B:
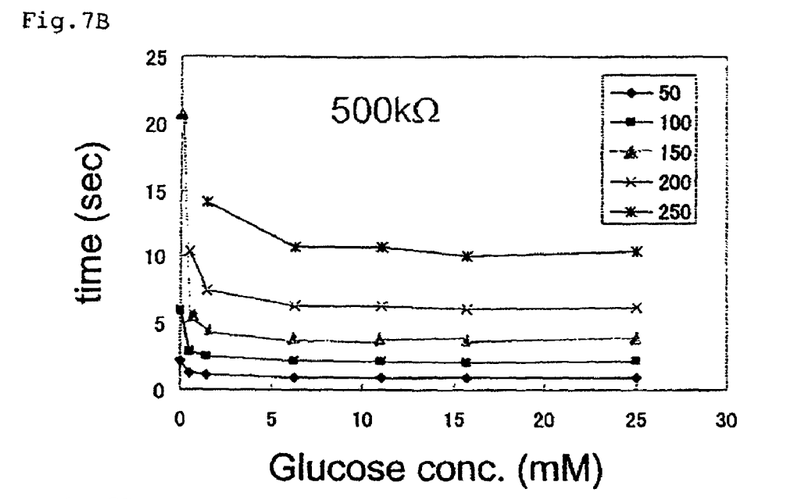
FIG. 7B shows the time required for charging of a capacitor for the change in the concentration of glucose (500 kΩ).
Figure 8A:
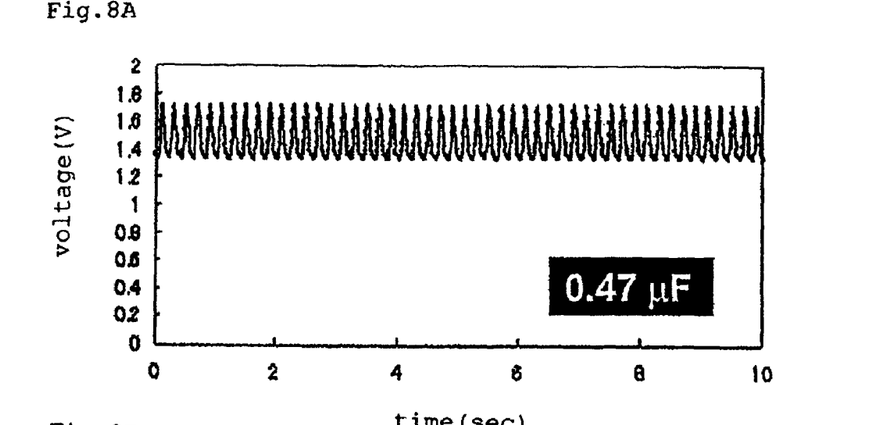
FIG. 8A shows the change in the electric potential of a capacitor by an enzyme fuel cell for time (0.47 µF).
Figure 8B:
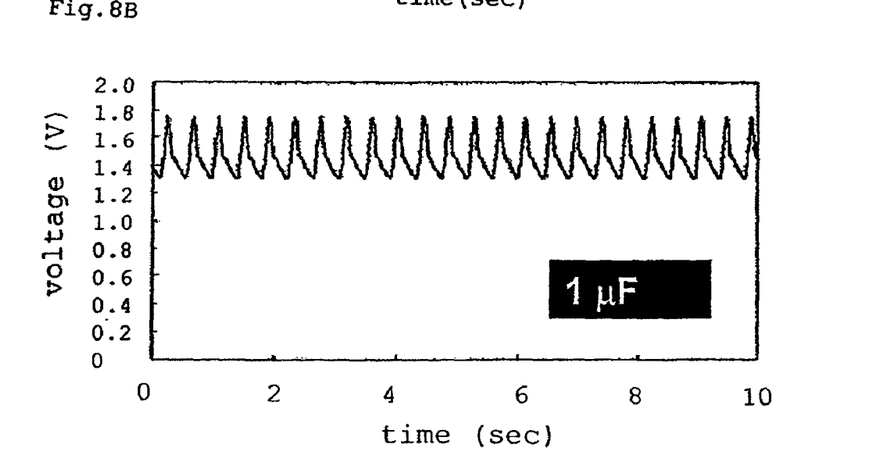
FIG. 8B shows the change in the electric potential of a capacitor by an enzyme fuel cell for time (1 µF).
Figure 8C:
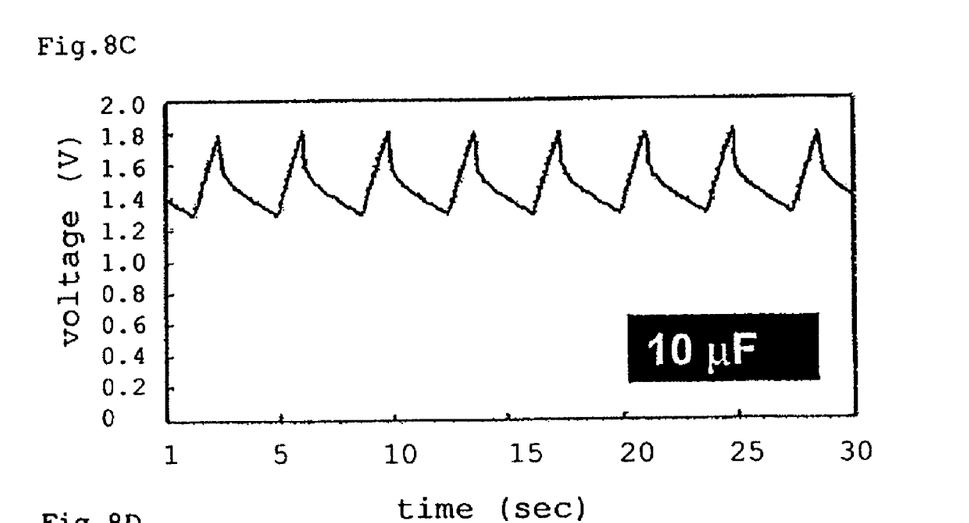
FIG. 8C shows the change in the electric potential of a capacitor by an enzyme fuel cell for time (10 µF).
Figure 8D:
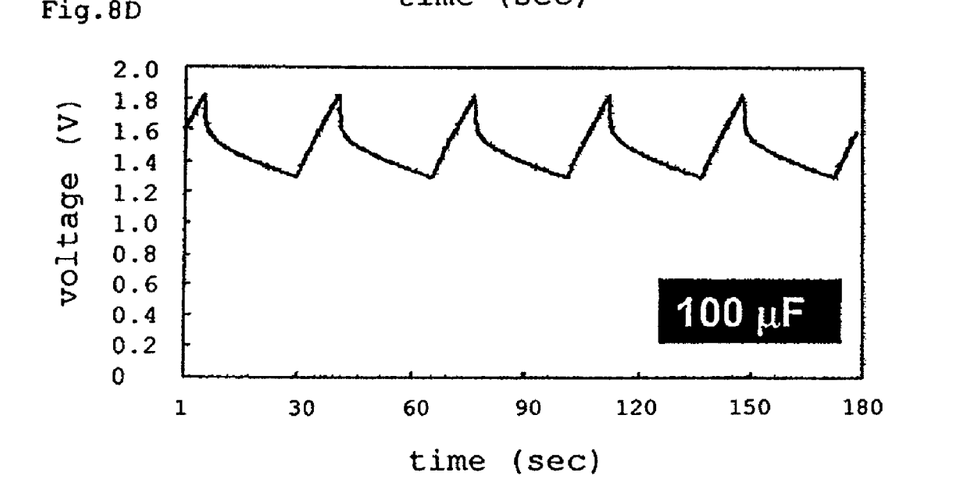
FIG. 8D shows the change in the electric potential of a capacitor by an enzyme fuel cell for time (100 µF).

The results are shown in FIG. 7. At a resistance of either 10 kΩ or 500 kΩ, as the glucose concentration increases, the charging time decreased. At 500 kΩ, the decrease in the charging time was scarcely observed with about 6 mM whereas, at 10 kΩ, an increase in the electric current was observed up to 11 mM. It was shown that, using the time for charging the capacitor as an index, the substrate concentration of an enzyme was able to be measured.

EXAMPLE 2

Preparation of Anode

Ketchen black ink (10 mL), 100 mM PPB (pH 7.0) (10 mL) and an FADGDH complex solution (40 mL) (4.2 U/mL) were mixed. And, 300 mL of the mixture was coated uniformly on 6 cm$^2$ of carbon cloth and then air-dried at 4° C. for 3 hours. By immersing the resultant in a 1% glutaraldehyde solution (10 ml) at room temperature for 30 minutes, a cross-linking treatment was carried out. Next, by immersing this carbon cloth in 10 mM Tris-HCl (10 ml) for 20 minutes, unreacted glutaraldehyde was removed. Thereafter, the resultant was immersed in 100 mM PPB (pH 7.0) (10 ml) for 1 hour to be equilibrated, thereby preparing an anode.

Preparation of Cathode:

A platinum supported carbon ink (60 mL) and 100 mM PPB (pH 7.0) (300 mL) were mixed. And, 300 mL of the mixture was uniformly coated on carbon cloth (6 cm$^2$) and the resultant was air-dried at 4° C. for 3 hours. To the resultant, 300 mL of 3% (w/v) Poly(dimethylsiloxane) (PDMS) diluted by ethanol was dropped and air-dried overnight to provide a cathode.

Figure 1:
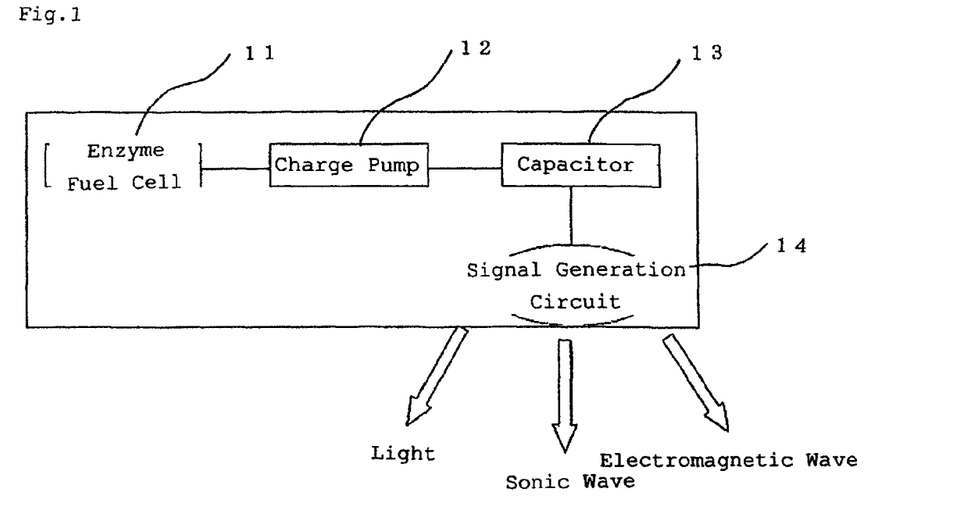
FIG. 1 shows a schematic view of the method for measuring a substrate and the apparatus therefor according to the present invention.

Construction of Electrical Cell and Circuit:

Using the prepared anode and cathode, an electrical cell was constructed using 100 mM PPB (pH7.0) as a reaction solution. A charge pump (boost IC; S-882Z18 manufactured by Seiko Instruments Inc.) capable of boosting from 0.3 V to 1.8 V was combined with this fuel cell, thereby constructing a circuit shown in FIG. 1. And, as a signal generation circuit, an orange light emitting diode was connected and various capacitors of 0.47 to 100 mF were further connected. By measuring the electric potential on the capacitor, and the emission interval and frequency of the light emitting diode, the charging and discharging cycle was evaluated.

Construction of Circuit Using Boost IC and Evaluation of Signal Frequency by Capacity of Capacitor Actuation of the present circuit by an enzyme fuel cell was evaluated by blinking of the light emission diode or by the change with time of the electric potential of the capacitor. And, a difference of the signal frequency obtained when the capacitor was replaced with ones of 0.47 to 100 mF was also evaluated. The concentration of glucose in a reaction solution was 20 mM.

The change with time of the electric potential of the capacitor in this case is shown in FIG. 8. When the capacitor of 0.47 mF was used, spike-like signals were observed at a frequency of five times per second (5/s). Also, at the same cycle, the blinking of the diode was observed. When the capacity of the capacitor was changed, the frequency of the signal changed. The cycle was 2.4/s, 0.27/s and 0.028/s when the capacitor of 1 mF, 10 mF and 100 mF was used, respectively. It was shown that the frequency of the signal was able to be, increased by making the capacity of the capacitor smaller.

Dependency of Capacitor Charge and Discharge Cycle on Glucose Concentration

Figure 9:
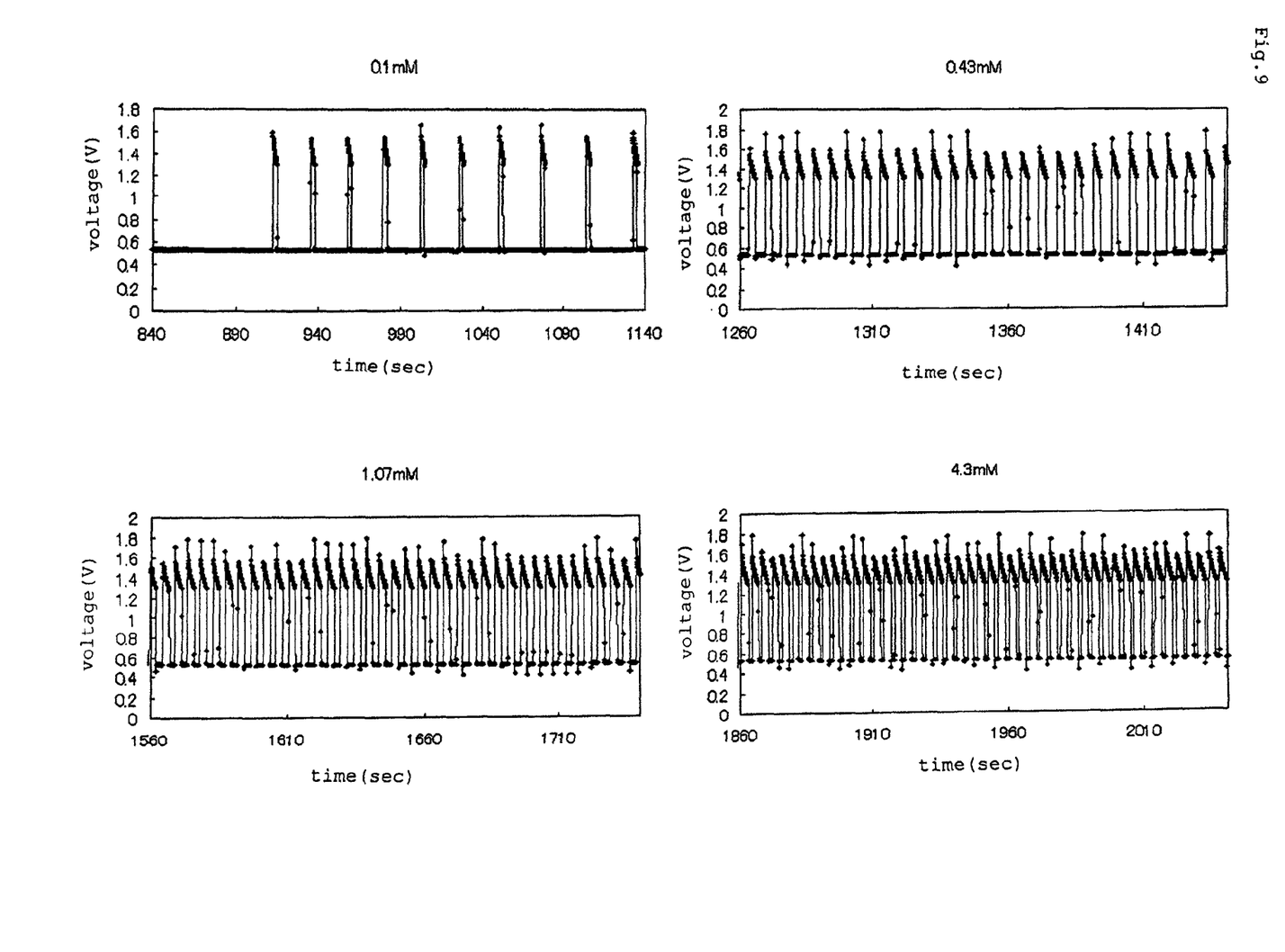
FIG. 9 shows the signal frequency in the case of changing the concentration of glucose.
Figure 10:
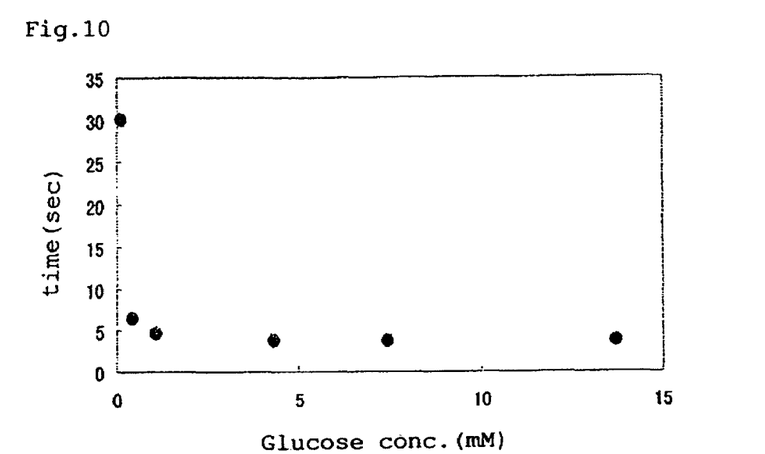
FIG. 10 shows the change in the time required for a capacitor reaching 1.8 V for the change in the concentration of glucose.
Figure 11:
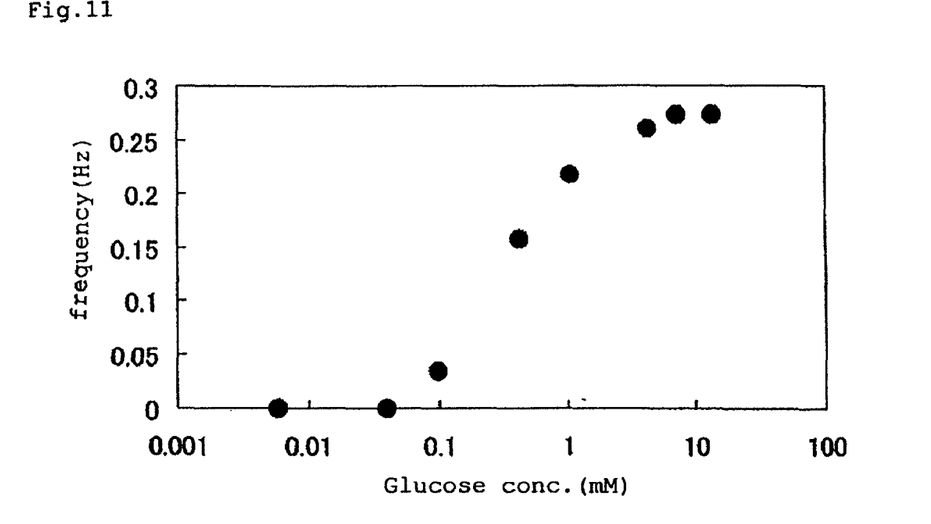
FIG. 11 The correlation of the frequency at which a capacitor reaches 1.8 V per unit time for the change in the concentration of glucose.

When the concentration of glucose which was an enzyme substrate was changed, the signal frequency obtained at that time was evaluated by blinking of the light emission diode or the change with time of the electric potential of the capacitor. As the capacitor, a capacitor of a capacity of 10 mF was used. The results are shown in FIG. 9. As the glucose concentration increases, the time required for the capacitor reaching a maximum electric potential became shorter, and an increase in the frequency at which it reached a peak electric potential per unit time was observed. Based on this result, the glucose concentration and the blinking of LED, that is, the time required for the capacitor reaching 1.8 V (FIG. 10) and the number of the blinking of LED per unit time, that is, the frequency at which the capacitor reached 1.8 V per unit time (FIG. 11) were determined. As shown in these curves, it was demonstrated that, from the obtained curve, the blinking of LED, that is, the time required for the capacitor reaching 1.8 V and the number of the blinking of LED per unit time, that is, the frequency at which the capacitor reached 1.8 V per unit time were dependent on the glucose concentration. From these, it was shown that the concentration of glucose was able to be measured by using the signal frequency as an index and a novel biosensor which used charging and discharging of the capacitor was constructed.

Actuation of Wireless System by Boosted Enzyme Fuel Cell

Using the prepared anode and cathode, an electrical cell was constructed using 100 mM PPB (pH7.0) as a reaction solution. A charge pump (boost IC; S-882Z18 manufactured by Seiko Instruments Inc.) capable of boosting from 0.3 V to 1.8 V or a charge pump (boost IC; S-882Z24 manufactured by Seiko Instruments Inc.) capable of boosting from 0.3 V to 2.4 V was combined with this fuel cell, thereby constructing a circuit shown in FIG. 1. As a signal generation circuit, a wireless system transmitter (infrared transmission) was connected. That is, a power supply part of the wireless transmitter was connected to a signal generation circuit shown in FIG. 1, thereby constructing a biosensor using, as an index, the actuation of the wireless transmission system by an electric potential discharged when the capacitor was charged. The concentration of glucose in the reaction solution was 0 to 25 mM.

As a result, in the presence of glucose, the wireless system transmitter was actuated and a signal was transmitted to a receiver at regular intervals.

Figure 12:
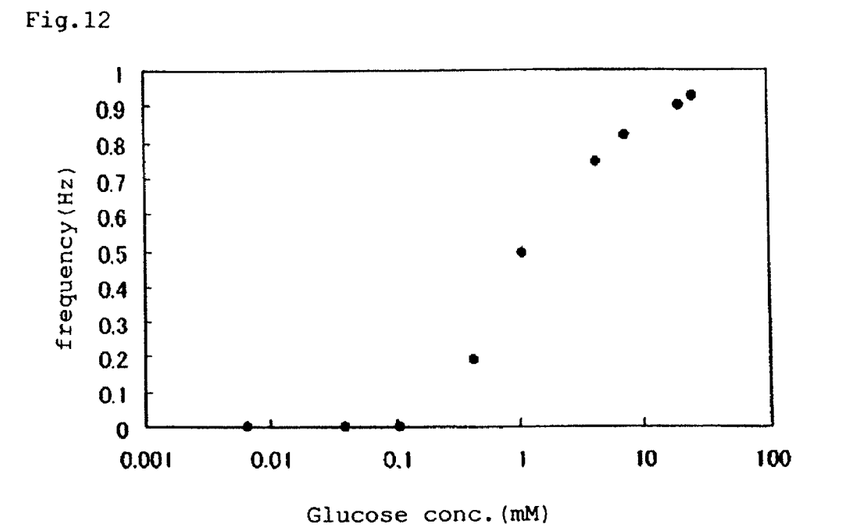
FIG. 12 The correlation between the frequency of an observed signal and the concentration of glucose in a wireless sensor (1.8 V boosting).
Figure 13:
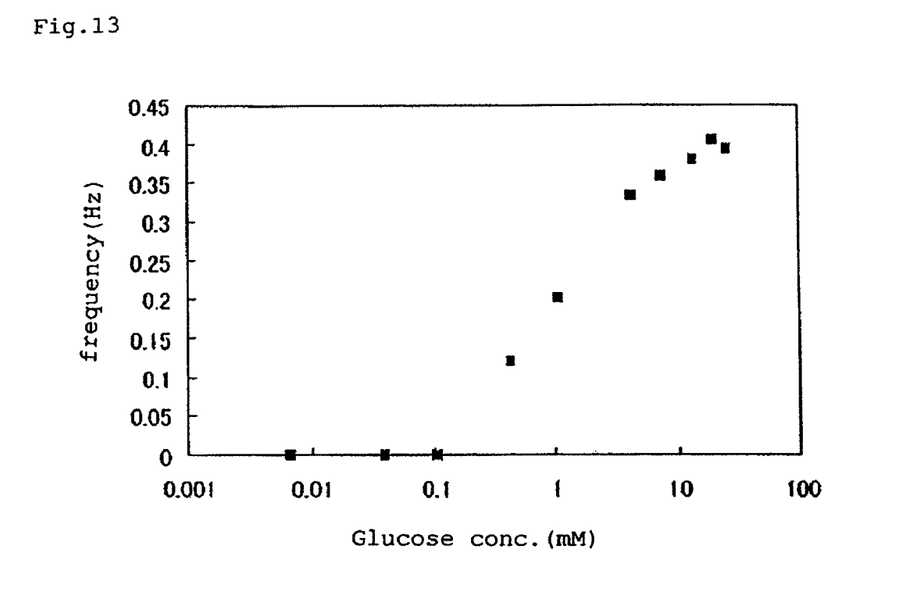
FIG. 13 The correlation between the frequency of an observed signal and the concentration of glucose in a wireless sensor (2.4 V boosting).
Figure 14:
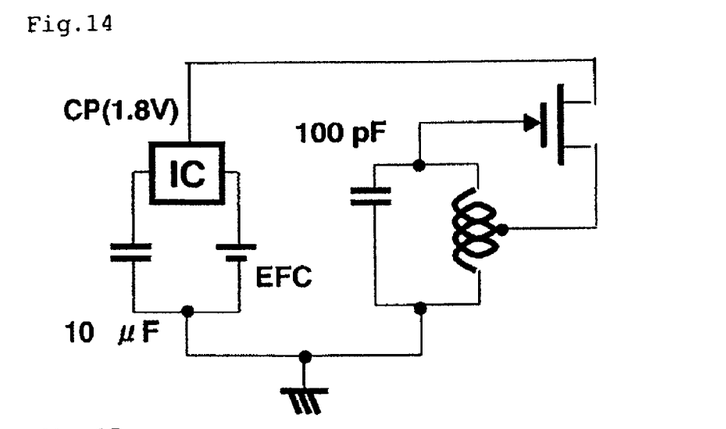
FIG. 14 shows an example, as a signal transmission circuit, of a measurement/transmission circuit using a resonant circuit as a transmitter.

FIG. 12 shows the correlation between the frequency of the signal observed at 1.8 V boosting and the glucose concentration. FIG. 13 shows the correlation between the frequency of the signal observed at 2.4 V boost and the glucose concentration. As shown here, at either boost, the reception frequency of the signal correlates with the glucose concentration and, by monitoring this frequency, the glucose concentration can be measured. The measurable concentration of glucose is, in either case, from 0.5 mM to 20 mM, which covers a range enough to measure a blood sugar value in diabetes mellitus. Thus, it is shown that it can be well applied to a blood sugar diagnostic apparatus including a continuous blood sugar diagnostic apparatus.

From this, it was shown that the wireless system was able to be actuated by using the electromotive force accumulated by the result of the enzyme reaction, which electromotive force is charged in the capacitor. Therefore, it was shown that, in the present novel biosensor, the wireless transmitter was applicable as the signal transmission circuit.

Figure 15:
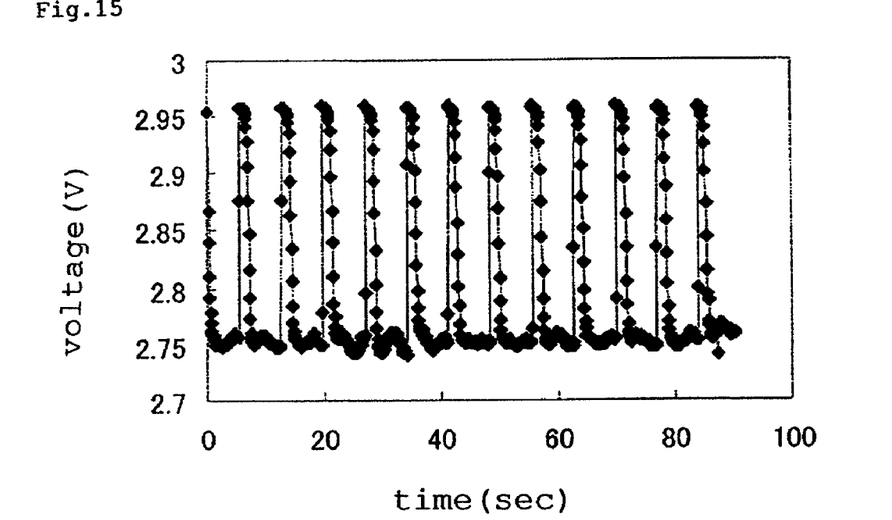
FIG. 15 shows an example in which an electromagnetic wave observed by using the transmission circuit shown in FIG. 14 was recorded.
Figure 16:
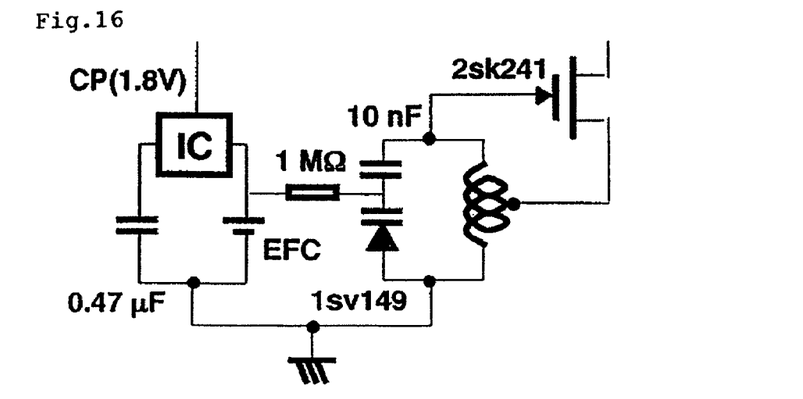
FIG. 16 shows an example, as a signal transmission circuit, of a measurement/transmission circuit using, as a transmitter, a resonant circuit using a varicap diode.

Construction of Measurement/Transmission Circuit Using Resonant Circuit as Transmitter A fuel cell was constructed in the same manner as described in Example 1 and a capacitor of 10 µF and a boost IC from 0.3 to 1.8 V were combined with this, thereby constructing a biocapacitor. As a power supply, an output power of the biocapacitor was connected to both ends, thereby producing a Hartley oscillation circuit. Using this transmitter, the reception frequency of an electromagnetic wave can be measured by a reception circuit. As a result, in the presence of glucose, as described in FIG. 15, it was observed that the electromagnetic wave was received at regular intervals. It is self explanatory, from the description thus far, that this reception frequency of the electromagnetic wave depends on the glucose concentration.

Figure 17:
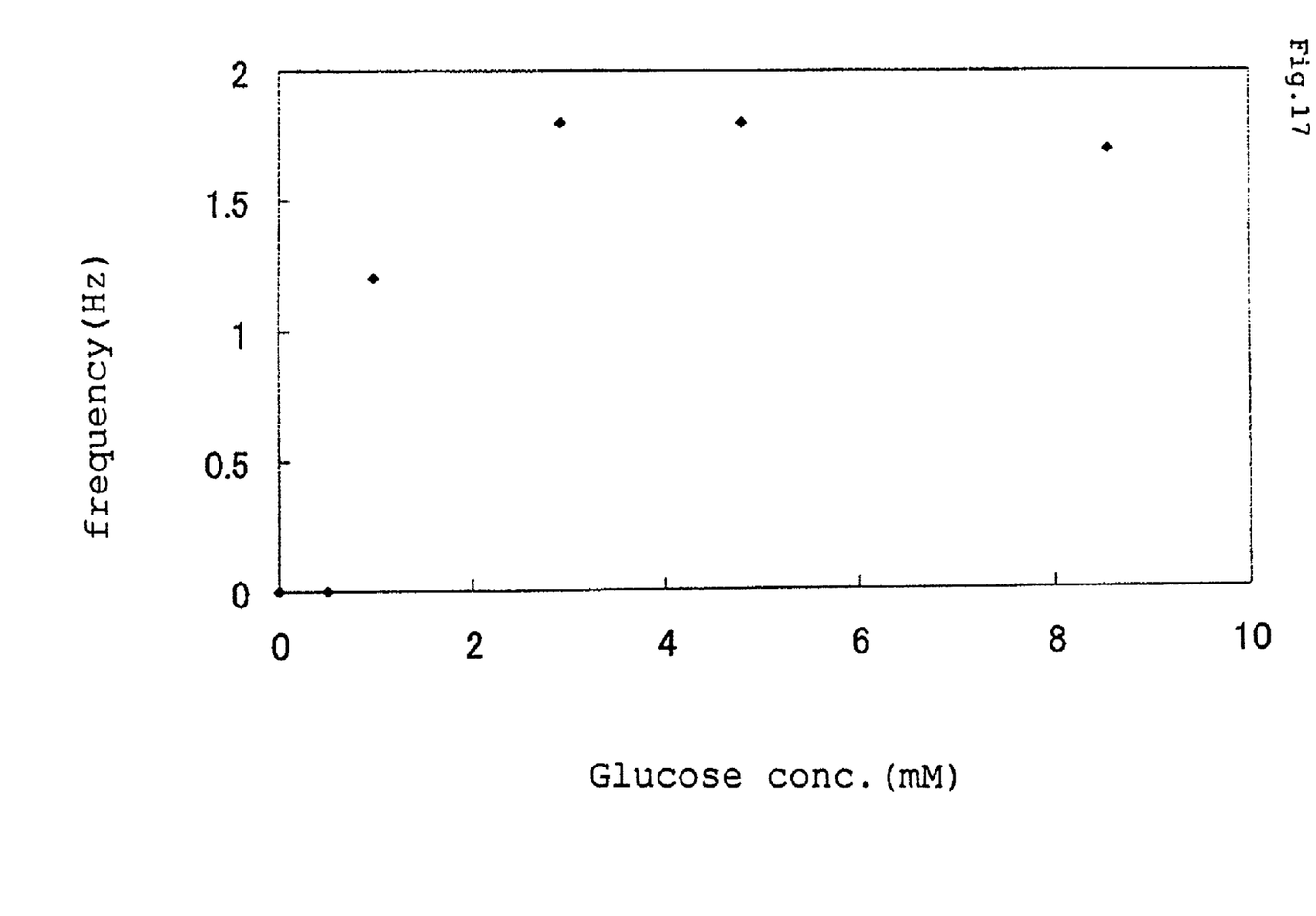
FIG. 17 shows an example in which an electromagnetic wave observed by using a transmission circuit shown in FIG. 16 and the concentration of glucose in a sample were measured.

Construction of Measurement/Transmission Circuit Using as Transmitter Resonant Circuit Using Varicap Diode A fuel cell was constructed in the same manner as described in Example 1 and a capacitor of 0.47 µF and a boost IC from 0.3 to 1.8 V were combined with this, thereby constructing a biocapacitor. As a power supply, an output power of the biocapacitor was connected to both the ends of a varicap (1sV149), thereby producing a Hartley oscillation circuit. Using this transmitter, the reception frequency of an electromagnetic wave can be measured by a reception circuit. FIG. 17 shows an example in which the frequency of the electromagnetic wave observed when using this transmission circuit and the concentration of glucose in samples were measured. As shown here, the concentration of glucose can be measured by using the present circuit.

What is claimed is:

1. An apparatus for measuring the concentration of a substrate, said apparatus comprising:
 a fuel cell having an anode on which a biocatalyst is disposed and a cathode on which an external electron acceptor is disposed;
 a capacitor connected to said fuel cell in series; and
 a measuring device for measuring said substrate concentration by using the charging rate of said capacitor as an index;
 wherein said measuring device measures the discharging frequency, by said capacitor discharging an accumulated electric potential when said electric potential charged in said capacitor reaches or exceeds a certain level;
 wherein said measuring device has a signal generation circuit generating a signal by said discharging from said capacitor and measures the frequency of said signal; and
 wherein an electromotive force generated by transferring electrons generated by a reaction between said substrate and said biocatalyst into said external electron acceptor on said cathode is charged in said capacitor, and the charging rate thereof is measured by said measuring device.

2. The apparatus according to claim 1, further comprising a charge pump for charging said capacitor, which charge pump boosts said electromotive force based on said biocatalytic reaction when said capacitor is charged.

3. The apparatus according to claim 1, wherein said signal generation circuit is a wireless transmitter.

4. The apparatus according to claim 1, wherein said measuring device measures a physical signal and/or a chemical signal generated when said signal generation circuit is actuated.

5. The apparatus according to claim 4, wherein said physical signal and/or said chemical signal are/is a sonic wave, light or an electromagnetic wave.

6. The apparatus according to claim 5, wherein said physical signal is an electromagnetic wave and a varicap diode is used for a transmission circuit of said electromagnetic wave.

7. The apparatus according to claim 1, wherein said measuring device further comprises a receiver for receiving said signal generated by said discharging of said capacitor when said capacitor exceeds the actuation voltage of said wireless transmitter by charging.

8. The apparatus according to claim 1, wherein said biocatalyst disposed on said anode is an enzyme.

9. The apparatus according to claim 8, wherein said enzyme is an oxidoreductase.

10. The apparatus according to claim 8, wherein said enzyme catalyzes oxidation of glucose.

* * * * *